(12) United States Patent
Herrenbauer et al.

(10) Patent No.: US 10,507,275 B2
(45) Date of Patent: Dec. 17, 2019

(54) TUBE SET FOR A BLOOD HANDLING APPARATUS AND BLOOD HANDLING APPARATUS COMPRISING A TUBE SET

(75) Inventors: Michael Herrenbauer, Neu-Anspach (DE); Robert Pohlmeier, Bad Homburg (DE); Andreas Laubrock, Wehrheim (DE); Angelika Bachmann, Rosbach v.d.H. (DE)

(73) Assignee: Fresenius Medical Care Deutschland GmbH, Bad Homburg (DE)

( * ) Notice: Subject to any disclaimer, the term of this patent is extended or adjusted under 35 U.S.C. 154(b) by 0 days.

(21) Appl. No.: 13/390,871

(22) PCT Filed: Aug. 13, 2010

(86) PCT No.: PCT/EP2010/004985
§ 371 (c)(1),
(2), (4) Date: Mar. 19, 2012

(87) PCT Pub. No.: WO2011/020585
PCT Pub. Date: Feb. 24, 2011

(65) Prior Publication Data
US 2012/0165718 A1 Jun. 28, 2012

(30) Foreign Application Priority Data
Aug. 19, 2009 (DE) .................. 10 2009 037 917

(51) Int. Cl.
*A61M 1/16* (2006.01)
(52) U.S. Cl.
CPC .................. *A61M 1/1656* (2013.01)
(58) Field of Classification Search
CPC .... A61M 25/00; A61M 2025/001–003; A61M 2025/0031; A61M 2025/1006;
(Continued)

(56) References Cited

U.S. PATENT DOCUMENTS 3,814,249 A * 6/1974 Eaton .............................. 210/86
4,391,599 A 7/1983 Jenkins
(Continued)

FOREIGN PATENT DOCUMENTS

EP 1110565 A2 6/2001
JP 2001526916 A 12/2001
(Continued)

OTHER PUBLICATIONS

International Search Report from PCT/EP2010/004985, dated Dec. 21, 2010.
(Continued)

*Primary Examiner* — Tan-Uyen T Ho
*Assistant Examiner* — Ned T Heffner
(74) *Attorney, Agent, or Firm* — Kilyk & Bowersox, P.L.L.C.

(57) ABSTRACT

A tube set for a blood handling apparatus, in particular an extracorporeal blood handling apparatus with an extracorporeal blood circuit or an apparatus for peritoneal dialysis, and a blood handling apparatus that has such a tube set are described. The tube set includes a device for collecting particles provided in a tube line portion of the tube set downstream of the tube portion placed in the occluding hose pump. The device for collecting particles prevents retention of solid substances that are possibly contained in the dialysis fluid, substituate or peritoneal solution. The tube set also has a device for limiting the pressure in the tube line portion between the occluding hose pump and the device for collecting particles. The device for limiting the positive pressure prevents an excessive positive pressure from building up in the tube line when fluid flow through the device for collecting particles is reduced or interrupted.

25 Claims, 5 Drawing Sheets

(58) Field of Classification Search
CPC .............. A61M 1/14; A61M 1/16; A61M 1/1601–1649; A61M 1/165; A61M 1/1654–1676; A61M 1/1678; A61M 1/28–288; A61M 1/3413–3417; A61M 1/342–3496; A61M 1/3643–3652
USPC ............ 604/4.01–6.01, 6.09–6.13, 9, 27, 28; 201/646, 741; 210/646, 741
See application file for complete search history.

(56) References Cited

U.S. PATENT DOCUMENTS

| | | | |
|---|---|---|---|
| 4,396,382 A | | 8/1983 | Goldhaber |
| 4,560,382 A | * | 12/1985 | Isono .................. 604/408 |
| 4,630,727 A | * | 12/1986 | Feriani et al. ............ 206/221 |
| 4,894,164 A | * | 1/1990 | Polaschegg ............ 210/646 |
| 5,032,265 A | * | 7/1991 | Jha et al. ............... 210/195.2 |
| 5,141,493 A | | 8/1992 | Jacobsen et al. |
| 5,429,483 A | * | 7/1995 | Tamari .................. 417/307 |
| 5,431,811 A | * | 7/1995 | Tusini et al. ............ 210/90 |
| 5,445,610 A | * | 8/1995 | Evert .................. 604/29 |
| 5,542,919 A | * | 8/1996 | Simon et al. ............ 604/29 |
| 5,605,545 A | | 2/1997 | Nowosielski et al. |
| 6,409,699 B1 | * | 6/2002 | Ash .................. A61M 1/1696 604/29 |
| 6,551,080 B2 | * | 4/2003 | Andersen et al. ........ 417/477.11 |
| 6,585,675 B1 | * | 7/2003 | O'Mahony et al. ........ 604/4.01 |
| 2002/0085952 A1 | * | 7/2002 | Ellingboe et al. ............ 422/45 |
| 2005/0082210 A1 | * | 4/2005 | Favre .................. 210/109 |
| 2008/0093276 A1 | * | 4/2008 | Roger .................. A61M 1/14 210/104 |
| 2009/0182263 A1 | | 7/2009 | Burbank et al. |

FOREIGN PATENT DOCUMENTS

| | | |
|---|---|---|
| JP | 2002-325840 A | 11/2002 |
| WO | 199922783 A1 | 5/1999 |
| WO | 02/35979 | 5/2002 |

OTHER PUBLICATIONS

Examination Report for Indian Patent Application No. 1451/DELNP/2012, issued by Intellectual Property India, date of dispatch Feb. 7, 2019, including Summary of the Report, 9 pages.

* cited by examiner

TUBE SET FOR A BLOOD HANDLING APPARATUS AND BLOOD HANDLING APPARATUS COMPRISING A TUBE SET

CROSS-REFERENCE TO RELATED APPLICATIONS

The present application is the national stage entry of International Patent Application No. PCT/EP2010/004985, filed on Aug. 13, 2010, and claims priority to Application No. DE 10 2009 037 917.7, filed in the Federal Republic of Germany on Aug. 19, 2009, each of which is expressly incorporated herein in its entirety by reference thereto.

FIELD OF INVENTION

The present invention relates to a hose set for an apparatus for blood treatment, in particular an apparatus for extracorporeal blood treatment with an extracorporeal blood circuit or an apparatus for peritoneal dialysis. Furthermore, the present invention relates to an apparatus for blood treatment, in particular an extracorporeal blood treatment apparatus or an apparatus for peritoneal dialysis, which comprises such a hose set.

BACKGROUND INFORMATION

Various methods for extracorporeal blood treatment are known. In an extracorporeal blood treatment, the patient's blood is cleaned in an extracorporeal blood circuit, which comprises a replacement unit, for example a dialyser or filter. The dialyser or filter comprises a blood chamber and a dialysing fluid chamber, which are separated by a semipermeable membrane. In haemodialysis in the narrower sense, blood flows through the blood chamber of the dialyser and dialysing fluid flows through the dialysing fluid chamber. In haemofiltration, the fluid withdrawn from the patient via the semipermeable membrane of the dialyser or filter is completely or partially replaced by a sterile substitution fluid (substituate), this being possible either upstream or downstream of the dialyser. Haemodialysis and haemofiltration can also be combined into one assembly, which is referred to as haemodiafiltration. These variants are referred to in the following as haemodialysis in the broader sense.

Apart from haemodialysis, peritoneal dialysis is also known, in which a peritoneal solution is fed to the patient's peritoneal space and is carried away from the peritoneal space via an implanted peritoneal catheter. In peritoneal dialysis, the blood treatment takes place through the peritoneal space.

In haemodialysis, the dialysis fluid can be made available with a central supply unit. The substituate can be obtained from fresh water and concentrate or from the dialysing fluid. In the case of acute haemodialysis, it is known to use dialysing fluid and substituate which is made available in bags. In order to make available dialysing fluid and substituate, multi-chamber bags are also known, which are filled with various constituents for the preparation of the dialysing fluid or the substituate. The individual constituents are usually mixed together for the preparation of the ready fluid only shortly before the treatment.

Known solution bags for the preparation of dialysing or substitution fluid comprise two separate chambers, whereof one chamber is filled with bicarbonate as an alkaline solution and the other chamber with an acid solution of calcium and electrolyte. The two chambers of the double-chamber bag enclosed by an outer packaging are separated by a separable seam. After removal of the bag from the outer packaging and separation of the seam, the two solutions are mixed to form a pH-value neutral dialysing or substitution fluid with an approximately physiological pH value. Depending on the embodiment, there is integrated in the primary packaging and/or the outer packaging a gas barrier which prevents outgassing of $CO_2$ from the bicarbonate solution and a resultant shift in the ph value to higher values. As a result of inappropriate storage and handling, however, damage to the packaging may occur, so that the pH value of the bicarbonate solution is shifted to higher values. In such a solution, precipitation of calcium carbonate in the ready dialysing or substitution fluid can occur as a solid constituent. The infusion of these particles then represents a threat to the patient.

The problem of the infusion of precipitating solid constituents also arises with peritoneal dialysis, in which the peritoneal solution is made available in a multi-chamber bag, which contains the constituents to be mixed together only shortly before the treatment. The peritoneal solution differs from the dialysing fluid essentially through the glucose content. Here too, inappropriate storage of or damage to the packaging can lead to precipitation of calcium carbonate as solid constituents, which may get into the patient's peritoneal space. Other undissolved substances or parts, for example splinters of break-off cones, may also be contained in the peritoneal solution.

The known blood treatment apparatuses comprise hose lines which are intended for one-off use. Such hose lines are offered as sets. The hose lines are inserted into occluding pumps, in particular roller pumps. Occluding pumps are also understood in the following to mean pump systems comprising a non-occluding pump, for example a centrifugal pump, with upstream and/or downstream valves, which are triggered by a control in such a way that the system of valve or valves and non-occluding pump behaves like an occluding pump.

Balancing devices are known in blood treatment for balancing fresh against consumed dialysing fluid. Balancing devices are known in which the bags, in which the fresh dialysing fluid is made available and the consumed dialysing fluid is received, are weighed. These balancing devices therefore comprise balances for the solution bags.

U.S. Pat. No. 5,605,545 describes a medical arrangement with bags for accommodating fluids, to which a hose line is connected which leads to a surgical instrument. The fluids from the bags are conveyed by an occluding hose pump. The hose set also comprises a bypass line, which bridges the hose section of the hose line inserted into the pump. Located in the bypass line is a non-return valve, which limits the pressure in the hose set to a specific level. An infusion line with a bypass line for pressure limitation is also known from U.S. Pat. No. 4,391,599.

A problem addressed by the present invention is to provide a hose set for an apparatus for blood treatment, in particular an extracorporeal blood treatment apparatus or an apparatus for peritoneal dialysis, which permits an operation of the blood treatment apparatus that is safe for the patient. Moreover, a problem addressed by the present invention is to provide a blood treatment apparatus, in particular an extracorporeal blood treatment apparatus or an apparatus for peritoneal dialysis, which offers increased safety for the patient.

SUMMARY

According to the present invention, a solution to the above-mentioned problems is described herein in connection with advantageous exemplary embodiments of the present invention.

The hose set according to the present invention for a blood treatment apparatus, in particular an extracorporeal blood treatment apparatus or an apparatus for peritoneal dialysis, comprises a device for trapping particles, which is provided in a hose line section of the hose line of the hose set that lies downstream of the hose section to be inserted into the occluding hose pump. The device for trapping particles prevents substances that may be precipitated or other solid constituents from being retained in the dialysing fluid, the substituate or the peritoneal solution. In this regard, the hose set according to the present invention is particularly advantageous for use in apparatuses for acute haemodialysis, in which the constituents required for the preparation of the dialysing fluid or the substituate are made available in multi-chamber bags, the outer packaging of which might be damaged as a result of inappropriate storage or handling.

Apart from the device for trapping particles, the hose set according to the present invention also comprises a device for limiting the pressure in the hose line section which lies between the hose section to be inserted into the occluding hose pump and the device for trapping particles. The device for limiting the overpressure prevents an excessive overpressure from building up in the hose line in the event of a reduced or interrupted fluid flow through the device for trapping particles.

If the hose set according to the present invention is used in the known apparatuses for acute haemodialysis, it can in some cases also contain a hose section which is used to heat the fluid conveyed by the hose set. The latter can be designed as a heating bag. The heating usually takes place in order to bring the temperature of the solution close to body temperature. The hose section for the heating can be located upstream or downstream of the occluding pump. The hose section for the heating is preferably located upstream of the hose pump. The device for limiting the overpressure prevents a part of the hose set downstream of the hose pump from bursting while the occluding hose pump is running. Thus, if the heating bag is nonetheless disposed downstream of the pump, the latter is thus likewise not able to burst due to an excessively high overpressure.

When a preset maximum overpressure is exceeded in a hose section which lies downstream of the hose section to be inserted into the occluding hose pump and upstream of the device for trapping particles, the device for limiting the overpressure creates a fluid connection between a hose section which lies downstream of the hose section to be inserted into the occluding hose pump and a hose section which lies upstream of the hose section to be inserted into the occluding hose pump. If the preset maximum overpressure is exceeded, a bypass line is thus created, through which the fluid can circulate when the occluding hose pump is running. When the preset maximum overpressure is no longer exceeded, the fluid connection is interrupted, so that the fluid can be conveyed by the occluding hose pump.

In a preferred embodiment, the device for limiting the overpressure comprises a prestressed non-return valve which, in the event of the preset maximum overpressure being exceeded, is opened in the direction of the fluid flow from the hose section downstream of the hose section to be inserted into the occluding hose pump to the hose section upstream of the hose section to be inserted into the occluding hose pump. When the preset maximum overpressure is no longer exceeded, the non-return valve is closed. The non-return valve can be connected to pieces of hose which branch off from the hose line immediately upstream and downstream of the hose section to be inserted into the occluding hose pump.

In an alternative embodiment, the device for limiting the overpressure comprises an electromagnetically, hydraulically or pneumatically actuated valve, which can be triggered by a control unit which cooperates with a device for detecting a malfunction due to a raised flow resistance through the device for trapping particles. The control unit is designed such that the valve is opened when a malfunction is detected, whereas the valve is closed when no malfunction is detected. The electromagnetically, hydraulically or pneumatically actuated valve can also be connected to hose pieces which branch off from the hose line.

The device for trapping particles is preferably a particle filter which has a pore size of 0.1 µm to 100 µm, preferably 0.2 µm to 50 µm, more preferably 0.2 µm to 20 µm. The particle filter can be fixedly connected to the hose sections of the hose line or by corresponding connection pieces to the hose line sections.

The hose set according to the present invention is used together with a bag for making available dialysing fluid or substituate for an extracorporeal blood treatment or making available a peritoneal solution for peritoneal dialysis. The bag can be connected to the hose line by suitable connection pieces. It is however also possible for the bag and the hose line to be already fixedly connected to one another.

The bag for making available dialysing fluid, substituate or peritoneal solution is preferably a multi-chamber bag, the chambers whereof are filled with various constituents for the preparation of the respective fluid. In particular, the bag is a double-chamber bag, the chambers whereof are separated from one another by a separable seam.

If the hose set according to the present invention is used for an extracorporeal blood treatment, the hose set can be used to convey the dialysing fluid, the hose line being inserted into the dialysing fluid pump. In an extracorporeal blood treatment, however, the hose set according to the present invention can also be used to convey the substituate, the hose line being inserted into the substituate pump. When the hose set is used for peritoneal dialysis, the hose line of the hose set is inserted into the occluding hose pump in order to convey the peritoneal solution.

A preferred embodiment of the apparatus for blood treatment, which can be an apparatus for extracorporeal blood treatment or an apparatus for peritoneal dialysis, provides a device for the detection of a malfunction due to a reduced or interrupted fluid flow through the device for trapping particles. In a particularly preferred embodiment, the device for detecting a malfunction cooperates with an alarm unit, which emits an optical and/or acoustic and/or tactile alarm in the event of a malfunction, in order to alert the user to the fact that, in order to avoid an excessively high overpressure in the hose line, the fluid circulates only in the bypass line while the occluding pump is running.

In a first preferred embodiment, the device for detecting a malfunction comprises an evaluation unit and a pressure transducer, which measures the pressure in the hose section which lies between the hose section to be inserted into the occluding hose pump and the device for trapping particles. The evaluation unit is designed such that the pressure measured with the pressure transducer is compared with a preset maximum overpressure. If the preset maximum overpressure is exceeded, the evaluation unit detects the malfunction. The electromagnetically or pneumatically actuated valve in the bypass line is then opened by the control unit, so that the fluid can circulate when the occluding pump is running.

An alternative embodiment of the device for detecting a malfunction provides an evaluation unit and a device for weighing a bag for accommodating dialysing fluid, substituate or peritoneal solution for the purpose of balancing the fluids. The evaluation unit is designed such that the reduction in weight of the bag within a preset time interval is compared with a preset threshold value. The preset threshold value corresponds to the reduction in weight of the bag to be expected when the fluid is conveyed with the desired delivery rate. If the flow of fluid through the device for trapping particles is reduced or interrupted, i.e. the particle filter has become partially or completely clogged, the reduction in weight falls below the preset threshold value. The evaluation unit then detects the malfunction.

Exemplary embodiments of the present invention will be explained in greater detail below, with reference to the accompanying drawings.

DETAILED DESCRIPTION

Figure 1:
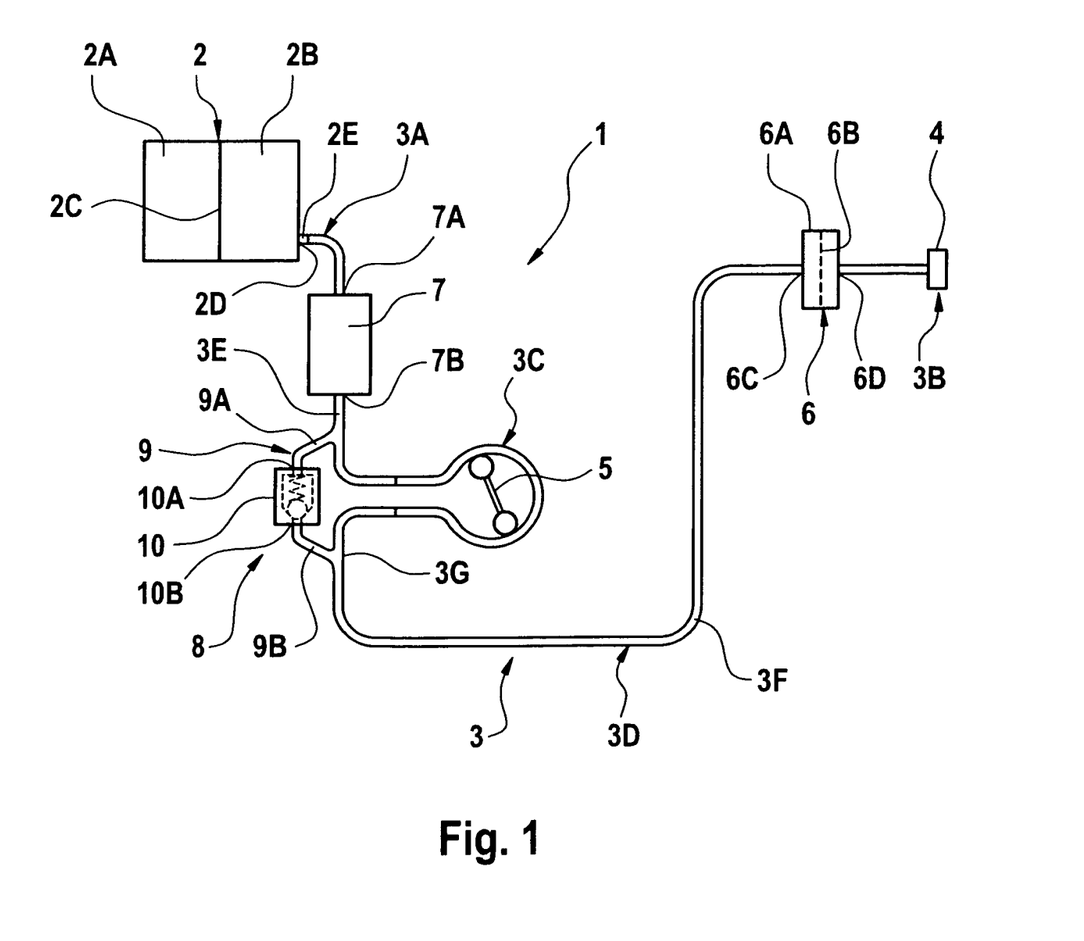
FIG. 1 shows an exemplary embodiment of the hose set according to the present invention for a blood treatment apparatus in a schematic representation.

FIG. 1 shows in a schematic representation an exemplary embodiment of the hose set according to the present invention, which in the present exemplary embodiment is intended for use in a device for acute haemodialysis. Hose set 1 comprises a bag 2 for making available the constituents required for preparing the dialysing fluid or the substituate in a hose line 3. In the present exemplary embodiment, bag 2 and hose line 3 are fixedly connected to one another. It is however also possible for bag 2 not to be part of the hose set, but for bag 2 and hose line 3 to be able to be connected to one another with suitable connectors.

Bag 2 is a double-chamber bag, which comprises a first chamber 2A and a second chamber 2B which are separated from one another by a separable seam 2C. First chamber 2A of bag 2 contains a bicarbonate-containing solution, whilst second chamber 2B contains a typically acid, calcium-containing solution. Both solutions are mixed together only shortly before the treatment after separation of seam 2C.

One end 3A of hose line 3 is connected to an outlet 2D of bag 2. Outlet 2D of bag 2 is closed by a closure part 2E, which is opened only shortly before the treatment. Other end 3B of hose line 3 comprises a connection piece 4, in order to allow the hose line to be connected to a corresponding connection piece at the inlet of the dialysing fluid chamber of a dialyser or to a drip chamber.

Hose line 3 is broken down into a plurality of hose sections. Hose line 3 comprises a hose section 3C, which can be inserted into an occluding hose pump 5, in the present exemplary embodiment into the dialysing fluid pump or substituate pump of an apparatus for acute haemodialysis. Dialysing-fluid or substituate pump 5 of the extracorporeal blood treatment apparatus is represented only schematically in FIG. 1.

A device 6 for trapping particles is located in hose section 3D of the hose line which lies downstream of hose section 3C to be inserted into occluding hose pump 5. This device is a particle filter 6. Particle filter 6 comprises a housing 6A, which is made for example from polycarbonate. Located in the housing is a filter membrane 6B with a pore size from 0.1 to 100 μm, preferably 0.2 to 50 μm, more preferably 0.2 to 20 μm. The membrane can be made from polyamide. Filter housing 6A comprises an inlet 6C and outlet 6D, which are fixedly connected to the hose line sections leading to filter 6 and leading away from the filter.

In the exemplary embodiment of FIG. 1, hose set 1 comprises a bag 7, which is used to heat the dialysing fluid to the patient's body temperature. Heating bag 7 is preferably located in line section 3E, which lies between bag 2 and hose section 3C to be inserted into hose pump 5. Heating bag 7 is therefore arranged upstream of hose pump 5. The heating bag can however also be arranged in hose section 3F downstream of hose section 3C to be inserted into hose pump 5 and upstream of particle filter 6. The heating bag comprises an inlet 7A and an outlet 7B, which is fixedly connected to the corresponding hose sections. For the purpose of heating the dialysing fluid or the substituate to body temperature, heating bag 7 is placed on a heating device (not shown) of the apparatus for acute haemodialysis.

Particle filter 6 retains particles which may be precipitated in the case of inappropriate storage of or damage to the packaging system, which is not completely represented in FIG. 1. If particle filter 6 has become partially or completely clogged, so that the flow resistance of the particle filter has significantly increased, an overpressure can build up in hose section 3F lying between hose pump 5 and particle filter 6 when hose pump 5 is running. Hose set 1 therefore comprises a device 8 for limiting the overpressure in hose line section 3F between hose pump 5 and particle filter 6.

Device 8 for limiting the overpressure comprises a bypass line 9 and a non-return valve 10, which is arranged in bypass line 9. Bypass line 9 comprises two hose pieces 9A and 9B. One hose piece 9A branches off from hose section 3E, which lies upstream of hose section 3C to be inserted into hose pump 5, and is connected to one connection 10A of non-return valve 10. Other hose piece 9B is connected to other connection 10B of non-return valve 10 and emerges into hose section 3G, which lies between hose section 3C to be inserted into hose pump 5 and particle filter 6.

Non-return valve 10 is preferably a spring-loaded non-return ball valve, which opens when a maximum preset overpressure is exceeded in the hose section downstream of pump 5 and upstream of filter 6 in the direction of bag 2, but otherwise is closed. In the event that particle filter 6 becomes clogged, non-return valve 10 opens when hose pump 5 is running, so that the fluid circulates via bypass line 9. This thus prevents the overpressure from increasing further when the pump is running as a result of which there is the risk of bursting of components downstream of the running pump, especially components of the device for trapping particles.

Hose set 1 according to the present invention can also comprise, apart from bag 2 for accommodating the dialysing fluid or the substituate and heating bag 7, further components which, for the sake of better clarity, are not represented in FIG. 1. For example, the hose set can contain further connection pieces. A drip chamber can also be a component part of the hose set when the hose set is used for supplying substitute. The hose set can however also be connected to a drip chamber, which is provided in the hose set of the extracorporeal blood circuit.

Figure 2:
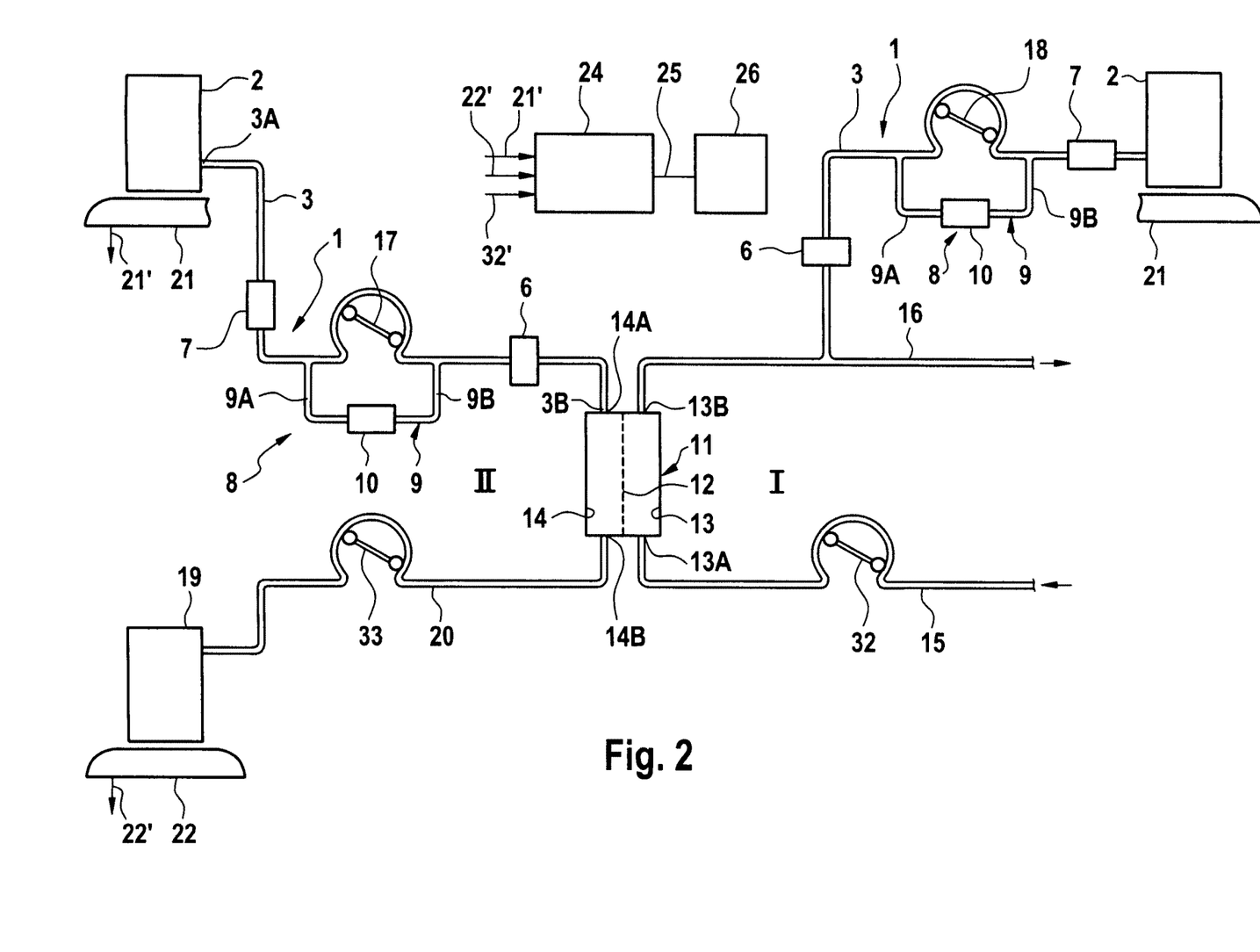
FIG. 2 shows an exemplary embodiment of the apparatus according to the present invention for extracorporeal blood treatment with a hose set according to the present invention in a very simplified schematic representation.

FIG. 2 shows the main components of an extracorporeal blood treatment apparatus with the hose set. In the present exemplary embodiment, it concerns an apparatus for acute haemodialysis, which is distinguished by the fact that dialysing fluid and/or substitute is made available in bags. FIG. 2 shows the main components of the apparatus only in a very simplified schematic representation.

The extracorporeal blood treatment apparatus comprises, as a replacement unit, a dialyser 11, which is divided by a semipermeable membrane 12 into a blood chamber 13 and a dialysing fluid chamber 14. Blood chamber 13 is part of an extracorporeal blood circuit I, whilst dialysing fluid chamber 14 is part of a fluid system II of the extracorporeal blood treatment apparatus.

An arterial blood line 15 leads from the patient to an inlet 13A of blood chamber 13. Blood pump 32 is used to convey the blood. A venous blood line 16 leads from outlet 13B of blood chamber 13 to the patient.

In the present exemplary embodiment of the apparatus for acute haemodialysis in the broader sense, the hose set described with reference to FIG. 1 is used to convey both dialysing fluid as well as substitute, for which reason the treatment method can more appropriately be referred to as haemodiafiltration. The same reference numbers are therefore used for hose set 1. In order to make dialysing fluid available, bag 2 of hose set 1 is filled with the constituents required for the preparation of the dialysing fluid, whilst for the preparation of substitute, bag 2 is filled with the constituents required for the preparation of the substitute. It can be essentially the same components as for the preparation of the dialysing fluid. In this regard, the two hose sets do not differ from one another in this exemplary embodiment.

Free end 3B of hose line 3 of hose set 1 for the dialysing fluid is connected to inlet 14A of dialysing fluid chamber 14 of dialyser 11, whilst free end 3B of hose line 3 of hose sets 1 for the substitute is connected to venous blood line 16. Free end 3B of hose line 3 can also be connected to arterial hose line 15. For the sake of better clarity, the representation of corresponding connection pieces has been dispensed with in FIG. 2. A drip chamber is likewise not represented in FIG. 2. Hose line 3 is inserted into dialysing fluid pump 17 for conveying the dialysing fluid and respectively into a substitute pump 18 for conveying substitute, which are a component of the blood treatment apparatus.

Both particle filters 6 effectively retain particles that may be precipitated. In the event that one of the two particle filters 6 should become clogged, respective non-return valve 10 opens, so that the dialysing fluid or the dialysate can circulate through bypass line 9, without the pressure in the respective hose line increasing above a preset maximum threshold value.

The consumed dialysing fluid is collected in a bag 19, which is connected via a hose line 20 to an outlet 14B of dialysing fluid chamber 14. Hose line 20 is usually inserted into a hose roller pump 33 (effluent pump), which is arranged downstream of dialysing fluid chamber 14.

Furthermore, the extracorporeal blood treatment apparatus comprises a device for weighing bags 2, 19, which comprises a common balance 21 for bag 2 for fresh dialysing fluid and substituate and a balance 22 for bag 19 for consumed dialysing fluid, on which the bags lie. Separate balances can however also be provided instead of a common balance for fresh dialysing fluid and substituate. Blood pump 32, hose roller pump 33 (effluent pump), dialysing fluid pump 17 and substituate pump 18 are triggered by a central control unit 24 via control lines (not shown), which receives the measurement values of balances 21, 22 via data lines 21', 22'.

Central control and computing unit 24 is connected via a data line 25 to an alarm unit 26, which emits an optical and/or acoustic and/or tactile alarm in the event of a malfunction.

Figure 3:
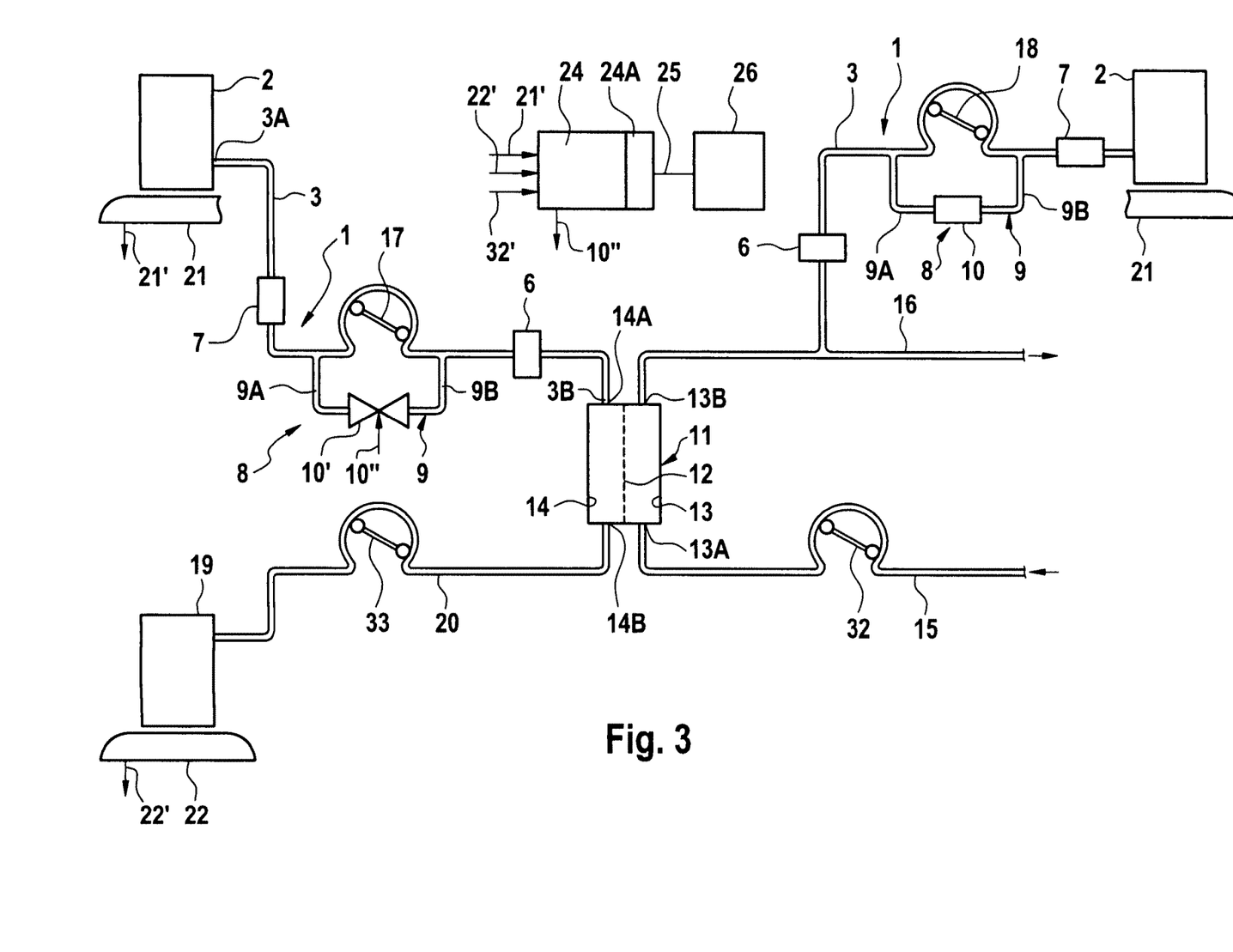
FIG. 3 shows a second exemplary embodiment of an apparatus according to the present invention for extracorporeal blood treatment with a hose set according to the present invention in a very simplified schematic representation.

FIG. 3 shows a second exemplary embodiment of the extracorporeal blood treatment apparatus in a very simplified schematic representation. The parts corresponding to one another are provided with the same reference numbers.

The extracorporeal blood treatment apparatus of FIG. 3 comprises a hose set 1 for dialysing fluid, wherein an electromagnetically actuated shut-off element 10' is provided in bypass line 9 instead of a non-return valve 10. Moreover, the blood treatment apparatus of FIG. 3 comprises a device for detecting a malfunction due to a reduced or interrupted fluid flow through particle filter 6 and a control unit for triggering electromagnetically actuated shut-off element 10'. The device for detecting the malfunction comprises an evaluation unit 24A and a device for weighing the bag for the dialysing fluid, the latter being balance 21 for weighing bag 2. Evaluation unit 24A is part of central control and computing unit 24 of the blood treatment apparatus, to which electromagnetic shut-off element 10' is connected via control line 10''. During the blood treatment, evaluation unit 24A of central control and computing unit 24 monitors the weight reduction of bag 2 in which the dialysing fluid is present. The weight reduction of the dialysing fluid in a preset time interval is compared by the evaluation unit with a preset threshold value. If the weight reduction per unit of time falls below the preset threshold value, the evaluation unit concludes that the fluid flow for particle filter 6 is reduced or interrupted, so that an inadmissibly high overpressure in hose line 2 builds up when dialysing fluid pump 17 is running. When this malfunction is detected, control and computing unit 24 generates an alarm signal, which is received by alarm unit 26 which is connected via data line 25 to control and computing unit 24. The alarm unit then emits an optical and/or acoustic and/or tactile alarm. At the same time, control and computing unit 24 opens electromagnetic shut-off element 10' in bypass line 9, so that the dialysing fluid can circulate. The preset threshold value for the weight reduction per unit of time should be selected such that the bypass line is opened when the preset maximum overpressure is exceeded in the hose line.

Figure 4:
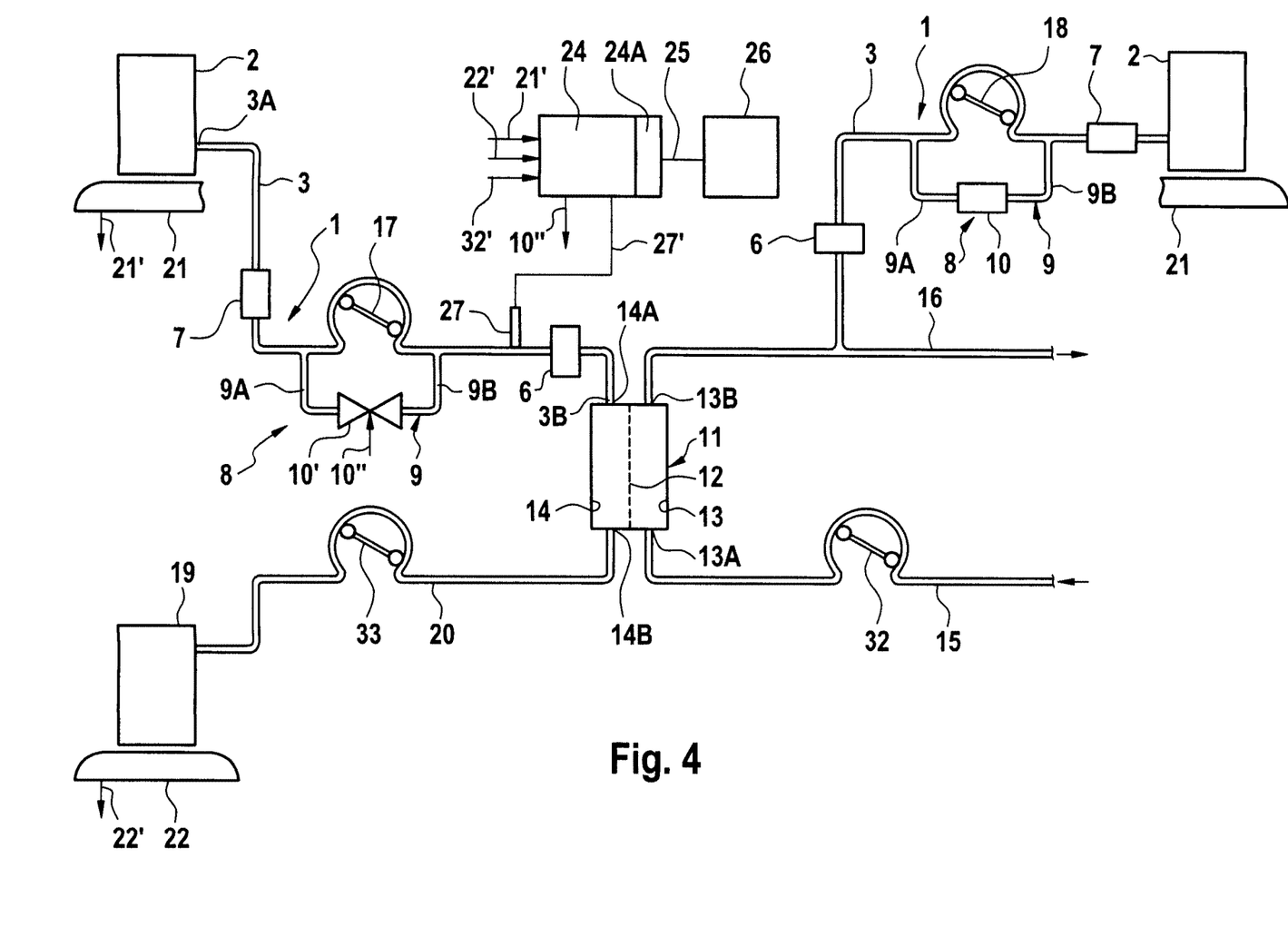
FIG. 4 shows a further exemplary embodiment of the extracorporeal blood treatment apparatus with a hose set according to the present invention in a very simplified schematic representation.

FIG. 4 shows a further exemplary embodiment of the extracorporeal blood treatment apparatus, which differs from the blood treatment apparatus described with reference to FIG. 3 by the fact that it is not the weight reduction of bag 2, but rather the pressure in hose line 3 of hose set 1 that is measured. The parts corresponding to one another are again provided with the same reference numbers.

In the blood treatment apparatus of FIG. 4, there is provided in hose set 1 for the dialysing fluid a pressure transducer 27 which is arranged in hose section 3F between hose section 3C, the latter to be inserted into blood pump 5, and particle filter 6. Pressure transducer 27 is connected via a data line 27' to central control and computing unit 24. In the event that a pressure is measured by pressure transducer 27 which exceeds the preset maximum overpressure, the malfunction is detected and an alarm is emitted. The weight reduction of bag 2 does not need to be monitored in this exemplary embodiment to detect a raised flow resistance through the particle filter.

FIGS. 2 to 4 show exemplary embodiments in which hose set 1 for the substitute does not comprise an electromagnetically or pneumatically actuated shut-off element 10', but rather a non-return valve 10. It is however also possible for the hose set for the substitute to comprise an electromagnetically, hydraulically or pneumatically actuated shut-off element, which is triggered by central control and computing unit 24.

Figure 5:
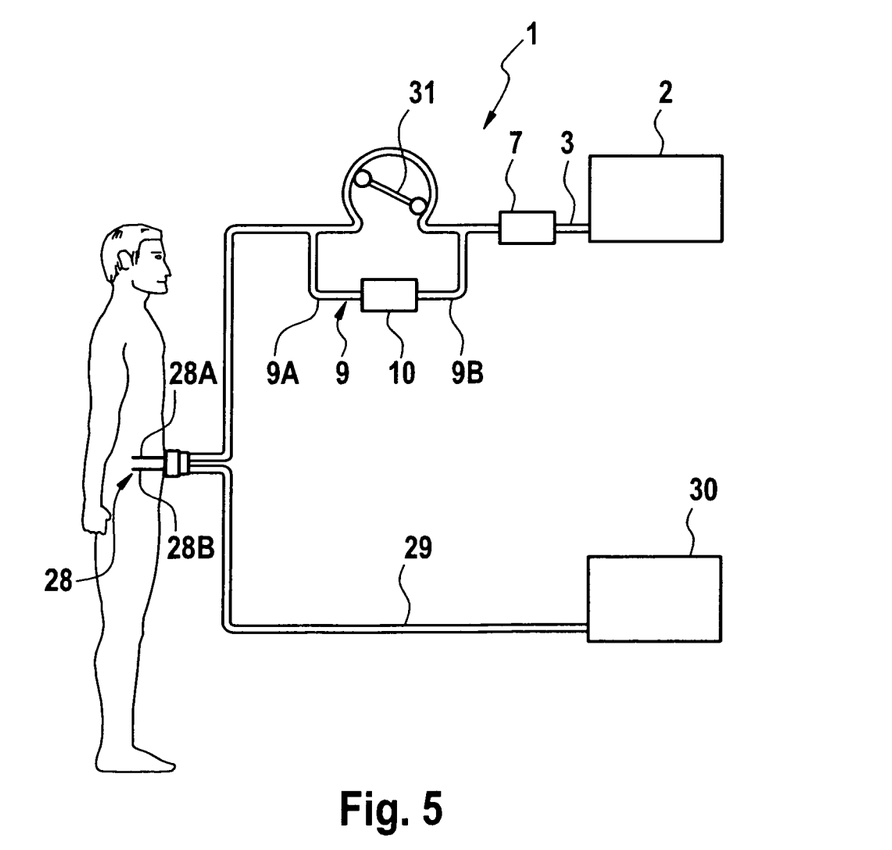
FIG. 5 shows an exemplary embodiment of an apparatus according to the present invention for peritoneal dialysis with a hose set according to the present invention in a very simplified representation.

FIG. 5 shows, in a very simplified schematic representation, an apparatus for peritoneal dialysis, in which hose set 1 described with reference to FIG. 1 is also used. For the use of the hose set in peritoneal dialysis, however, bag 2 is not filled with the constituents required for the preparation of a dialysing fluid, but rather those required for a peritoneal solution. Otherwise, the hose sets do not however differ from one another. The parts corresponding to one another are therefore again provided with the same reference numbers. The apparatus for peritoneal dialysis comprises hose set 1 according to the present invention, wherein free end 3B of hose line 3 is connected to first lumen 28A of a double-lumen peritoneal catheter 28 for supplying peritoneal solution into the peritoneal space or carrying away the solution from the peritoneal space of the patient. Connected to second lumen 28B of peritoneal catheter 28 is a hose line 29, which leads to a bag 30 for collecting peritoneal solution. Hose line 3 of the hose set is inserted into an occluding hose pump 31 of the apparatus for peritoneal dialysis.

Particle filter 6 of hose set 1 again retains precipitating particles which may be contained in the peritoneal solution in the case of inappropriate storage of or damage to the packaging system of bag 2. Here too, the exceeding of a maximum preset overpressure when the hose pump is running is again prevented when the particle filter becomes clogged.

The invention claimed is:

1. An arrangement comprising:
    a bag containing, in solution, constituents for a dialysing fluid, a substitute, or a peritoneal solution, the constituents comprising bicarbonate in solution and calcium in solution, wherein interaction between the bicarbonate and calcium in the solution causes the precipitation of calcium carbonate particles; and
    a hose set comprising a hose line having a first end, a second end, an occluding hose section, and a downstream hose section, wherein (i) the occluding hose section is configured to be inserted into an occluding hose pump of a blood treatment apparatus, (ii) the bag and the hose line are fixedly connected to one another at the first end of the hose line, or the bag and the hose line are adapted to be connected to one another with connectors, and (iii) the downstream hose section is located downstream of the occluding hose section in the hose line, the hose set further comprising:
    a device for trapping the calcium carbonate particles, the device being a particle filter, situated in the downstream hose section, comprising a single inlet and a single outlet, and configured to enable fresh dialysing fluid, substitute, or a peritoneal solution to pass through while retaining particles from the fresh dialysing fluid, substitute, or peritoneal solution, thus making available, downstream of the device for trapping the calcium carbonate particles, (1) dialysing fluid or substitute for an extracorporeal blood treatment, or (2) a peritoneal solution for peritoneal dialysis, wherein a hose line section downstream and leading away from the device for trapping the calcium carbonate particles includes the second end of the hose line;
    a device for limiting overpressure in the downstream hose section when the device for trapping the calcium carbonate particles is partially or completely clogged, the device for limiting overpressure configured such that when a preset maximum overpressure is exceeded in the downstream hose section downstream of the occluding hose section and upstream of the device for trapping the calcium carbonate particles due to the partially or completely clogged device for trapping the calcium carbonate particles, a fluid connection is created in a bypass line between the downstream hose section downstream of the occluding hose section and an upstream hose section upstream of the occluding hose section, and the fluid connection is interrupted when the preset maximum overpressure is no longer exceeded; and
    a dialyzer, a peritoneal catheter, or an arterial or venous blood line of an extracorporeal blood circuit, connected to the second end of the hose line, and downstream of the second end of the hose line, wherein
    the downstream hose section connects the occluding hose section to the device for trapping the calcium carbonate particles, and the hose set is configured for making available dialysis fluid or substitute for an extracorporeal blood treatment or for making available a peritoneal solution for peritoneal dialysis.

2. The arrangement according to claim 1, further comprising:
    a heating bag for heating fluid flowing through the hose line, the heating bag being located upstream of the device for trapping the calcium carbonate particles.

3. The arrangement according to claim 1, wherein the bag is a multi-chamber bag having at least two chambers containing the constituents for the dialysing fluid, the substituate, or the peritoneal solution, the multi-chamber bag comprising:
    a first chamber comprising the bicarbonate in solution; and
    a second chamber comprising the calcium in solution as an acid, calcium-containing solution.

4. The arrangement of claim 1, wherein the bag is a multi-chamber bag having at least two chambers containing the constituents, the constituents are for preparation of a peritoneal solution, the two chambers are separated by a separable seam, and the multi-chamber bag comprises:
    a first chamber comprising the bicarbonate in solution; and
    a second chamber comprising the calcium in solution as an acid, calcium-containing solution.

5. The arrangement according to claim 1, wherein the dialyzer, peritoneal catheter, or arterial or venous blood line of an extracorporeal blood circuit, connected to the second end of the hose line, comprises a dialyzer connected to the second end of the hose line, and
    the hose set is configured for making available dialysis fluid for haemodialysis.

6. The arrangement according to claim 1, wherein the dialyzer, peritoneal catheter, or arterial or venous blood line of an extracorporeal blood circuit, connected to the second end of the hose line, comprises a peritoneal catheter connected to the second end of the hose line, and
    the hose set is configured for making available a peritoneal solution for peritoneal dialysis.

7. The arrangement according to claim 1, wherein the dialyzer, peritoneal catheter, or arterial or venous blood line of an extracorporeal blood circuit, connected to the second end of the hose line, comprises an arterial or venous blood line of an extracorporeal blood circuit, connected to the second end of the hose line, and
the hose set is configured for making available substitute for an extracorporeal blood treatment.

8. The arrangement according to claim 1, wherein the device for trapping the calcium carbonate particles is a particle filter having a pore size of from 0.1 µm to 100 µm.

9. The arrangement according to claim 8, wherein the device for trapping the calcium carbonate particles is a particle filter having a pore size of from 0.2 µm to 50 µm.

10. The arrangement according to claim 9, wherein the device for trapping the calcium carbonate particles is a particle filter having a pore size of from 0.2 µm to 20 µm.

11. An apparatus for blood treatment, comprising:
an arrangement according to claim 1.

12. The apparatus for blood treatment according to claim 11, wherein the blood treatment apparatus is an apparatus for peritoneal dialysis, wherein the bag contains, in solution, constituents for a peritoneal solution, and wherein the apparatus having an inlet line for supplying the peritoneal solution and an outlet line for carrying away the peritoneal solution in the form of filtered peritoneal solution available for peritoneal dialysis;
wherein the hose line of the hose set is the inlet line for supplying the peritoneal solution, and
wherein the hose line of the hose set is configured to be inserted into the occluding hose pump of the apparatus for peritoneal dialysis in order to convey the peritoneal solution.

13. The apparatus for blood treatment according to claim 12, wherein the bag is a multi-chamber bag having at least two chambers containing the constituents and the constituents are for preparation of the peritoneal solution, the multi-chamber bag comprising:
a first chamber comprising the bicarbonate in solution; and
a second chamber comprising the calcium in solution as an acid, calcium-containing solution.

14. The apparatus for blood treatment according to claim 11, wherein the blood treatment apparatus is an apparatus for extracorporeal blood treatment, the apparatus further comprising:
a replacement unit comprising a first chamber configured as part of an extracorporeal blood circuit, and a second chamber configured as part of a fluid system;
wherein the extracorporeal blood circuit comprises an arterial blood line leading to an inlet of the first chamber of the replacement unit, and a venous blood line leading away from an outlet of the first chamber of the replacement unit.

15. The apparatus according to claim 14 wherein the bag is a multi-chamber bag having at least two chambers containing the constituents and the constituents are for preparation of a dialysing fluid, the multi-chamber bag comprising:
a first chamber comprising the bicarbonate in solution; and
a second chamber comprising the calcium in solution as an acid, calcium-containing solution;
wherein an inlet of the second chamber of the replacement unit is connected to the second end of the hose line; and
wherein the occluding hose section is configured to be inserted into the occluding hose pump of the extracorporeal blood treatment apparatus in order to convey the dialysing fluid.

16. The apparatus according to claim 14, wherein the bag is a multi-chamber bag having at least two chambers containing the constituents and the constituents are for preparation of a substituate, the multi-chamber bag comprising:
a first chamber comprising the bicarbonate in solution; and
a second chamber comprising the calcium in solution as an acid, calcium-containing solution;
wherein one of the arterial blood line and the venous blood line of the extracorporeal blood circuit is connected to the second end of the hose line; and
wherein the occluding hose section configured to be inserted into the occluding hose pump is inserted into a substituate pump of the extracorporeal blood treatment apparatus.

17. The apparatus according to claim 11, further comprising:
a device configured to detect a malfunction due to one of a reduced and interrupted fluid flow through the device for trapping the calcium carbonate particles.

18. The apparatus according to claim 17, wherein the device configured to detect the malfunction cooperates with an alarm unit that emits at least one of an optical, acoustic and tactile alarm when the malfunction is detected.

19. The apparatus according to claim 17, wherein the device configured to detect the malfunction comprises an evaluation unit and a pressure transducer that measures a pressure in a measuring hose section between the occluding hose section and the device for trapping the calcium carbonate particles; and
wherein the evaluation unit is configured such that the pressure measured with the pressure transducer is compared to a preset maximum overpressure, the malfunction being detected when the preset maximum overpressure is exceeded.

20. The apparatus according to claim 17, wherein the device configured to detect the malfunction comprises an evaluation unit and a device for weighing the bag; and
wherein the evaluation unit is configured such that a reduction in weight of the bag within a preset time interval is compared with a preset threshold value, the malfunction being detected when the reduction in weight falls below the preset threshold value.

21. The arrangement according to claim 1, wherein the device for limiting the overpressure comprises a prestressed non-return valve which, in the event of the preset maximum overpressure being exceeded, is opened in a direction of fluid flow through the bypass line from the downstream hose section to the upstream hose section, and is closed when the preset maximum overpressure is no longer exceeded.

22. The arrangement according to claim 21, wherein the bypass line comprises a first hose piece, an end of which is connected to one connection of the prestressed non-return valve, branches off from the downstream hose section, and a second hose piece, an end of which is connected to another connection of the prestressed non-return valve, branches off from the upstream hose section.

23. The arrangement according to claim 21, wherein the prestressed non-return valve is configured to open when the preset maximum overpressure is exceeded in the downstream hose section downstream of the occluding hose section and upstream of the device for trapping the calcium carbonate particles.

24. The arrangement according to claim 1, wherein the device for limiting the overpressure comprises one of an electromagnetically, hydraulically and pneumatically actuated valve configured to be triggered by a control unit cooperating with a device for detecting a malfunction due to a raised flow resistance through the device for trapping the calcium carbonate particles, wherein the control unit is configured to open the valve when the malfunction is detected, such that the fluid connection is created in the bypass line between the downstream hose section and the upstream hose section, and to close the valve when no malfunction is detected.

25. The arrangement according to claim 24, wherein the bypass line comprises a first hose piece, an end of which is connected to one connection of the one of the electromagnetically, hydraulically and pneumatically actuated valve, branches off from the downstream hose section, and a second hose piece, an end of which is connected to another connection of the one of the electromagnetically, hydraulically and pneumatically actuated valve, branches off from the upstream hose section.

* * * * *